(12) United States Patent
Handa et al.

(10) Patent No.: US 6,670,459 B2
(45) Date of Patent: Dec. 30, 2003

(54) PROCESS FOR THE ISOLATION OF NOVEL OLIGOSPIROSTANOSIDE

(75) Inventors: Sukhdev Swami Handa, Jammu (IN); Om Prakash Suri, Jammu (IN); Vishwa Nath Gupta, Jammu (IN); Krishan Avtar Suri, Jammu (IN); Naresh Kumar Satti, Jammu (IN); Vikram Bhardwaj, Jammu (IN); Kasturi Lal Bedi, Jammu (IN); Anamika Khajuria, Jammu (IN); Anpurna Kaul, Jammu (IN); Girish G. Parikh, Maharashtra (IN); Prabhakar Kulhar, Maharashtra (IN); Ulhas Salunkhe, Maharashtra (IN); Raman Krishnamurthy, Maharashtra (IN)

(73) Assignee: Zandu Pharmaceutical Works Ltd., Maharashtra (IN)

( * ) Notice: Subject to any disclaimer, the term of this patent is extended or adjusted under 35 U.S.C. 154(b) by 0 days.

(21) Appl. No.: 10/103,633

(22) Filed: Mar. 20, 2002

(65) Prior Publication Data

US 2003/0181395 A1 Sep. 25, 2003

(51) Int. Cl.$^7$ .............................................. C07H 15/24
(52) U.S. Cl. ............................ 536/5; 514/26; 514/824; 536/124; 536/128; 536/123.3; 536/6
(58) Field of Search ...................... 536/5, 6, 6.1, 124, 536/123.3, 128; 514/26, 824

(56) References Cited

PUBLICATIONS

Biochemical Nomenclature And Related Documents : Spirostans, (Portland Press, London, second edition, 1992, XP–002210388.*
PCT International Search Report.
Shvets, S.A., et al., "Steroidal Glycosides of Nicotiana Tabacum Seeds. II Structure of Nicotianosides C and F", *Chemical Abstracts*, 124 (17):847, 1996, Columbus, Ohio, US; Abstract No. 226557; XP–002210389; Khim. Prir. Soedin. 1995, (3):396–401 (Russ).

Muruganandan, S., et al., "Studies on the Immunostimulant and Antihepatotoxic Activities of Asparagus Racemosus Root Extract", *Journal of Medicinal and Aromatic Plant Sciences*, 22–23 (4A–1A):49–52, Oct.–Mar., 2000–2001; Data Base Accession No. PREV200100341263, XP–002210438.
Ravikumar, P.R., et al., "Chemistry of Ayurvedic Crude Drugs: Part VI$^A$ –(Shatavari–1): Structure of Shatavarin–I-V$^{b,c}$", *Indian Journal of Chemistry*, 26B:1012–1017, Nov. 1987, XP–001096221.
Iubmb (Liebecq, C.), *Biochemical Nomenclature And Related Documents:Spirostans*, (Portland Press, London, 2$^{nd}$ Edition, 1992), p. 203, XP–002210388.
U.K. Kanitkar et al., *J. Res. Indian Med.*, 1969, 3:123–137.
G.V. Satyavati et al., *Medicinal Plants of India*, 1976, vol. 1, 101–106.
P.R. Ravikumar et al., *Indian J. Chem*, 1987, 26B:1012–1017.
Dipak Kumar Kar et al., *Cell and Chromosome Res.*, 1984, 7(4):10–15.
T. Sekine et al, *Chem Pharm Bull.*, 1994:42(6):1360–1362.
T. Sekine et al, *Phytochemistry*, 1997, 44(4):763–764.
S. Kiyosawa et al., *Chem Pharm Bull.*, 1968, 16(6):1162–1164.
Gong Wu et al., *Phytochemistry*, 1996, 42(6):1677–1681.
X.C. Li et al., *Phytochemistry*, 1990, 29(12):3899–3901.
S. Soe et al, *J. Am. Chem. Soc.*, 1978, 100(11):3331–3339.
S. Hakomori, *J. Biochem*, 1964, 55(2) 205–208.

* cited by examiner

*Primary Examiner*—James O. Wilson
*Assistant Examiner*—Ganapathy Krishnan
(74) *Attorney, Agent, or Firm*—Morgan & finnegan, LLP

(57) ABSTRACT

The present invention relates to a process for the isolation of a novel oligospirostanoside structurally constructed as 3-0-[α-L-rhamnopyranosyl-(1→2)-α-L-rhamnopyranosyl-(1→4)-0-β-D-glucopyranosyl]-25(S)-5β spirostan-3β-ol isolated from *Asparagus racemosus* and biologically evaluated as a potent immunomodulatory agent.

6 Claims, No Drawings

US 6,670,459 B2

PROCESS FOR THE ISOLATION OF NOVEL OLIGOSPIROSTANOSIDE

FIELD OF THE INVENTION

The present invention relates to a process for the isolation of a novel oligospirostanoside from *Asparagus racemosus* and to the novel oligospirostanoside obtained by said process. The present invention particularly relates to a novel chemical entity oligospirostanoside (hereinafter referred to as Immunoside) and structurally constructed as 3-0-[α-L-rhamnopyranosyl-(1→2)-α-L-rhamnopyranosyl-(1→4)-0-β-D-glucopyranosyl]-25(S)-5α-spirostan-3β-ol (on the basis of IR, $^1$H and $^{13}$C—NMR Data (CPD, DEPT, HOMOCOR, HETCOR and COLOC), isolated from *Asparagus racemosus* and biologically evaluated as a potent immunomodulatory agent.

The present invention also relates to a pharmaceutical composition containing the novel oligospirostanoside and to a method for immunomodulation using said oligospirostanoside

BACKGROUND OF THE INVENTION

The Ayurvedic crude drug, Shatavari comprises decorticated roots of *Asparagus racemosus* wild [Kanitkar, U. K., Dange, P. S. and Pendse, G. S. *J. Res. Indian Med.* 3 (1969) 123; *Medicinal Plants of India* vol. 1, ed. by Satyavati, G. V., Raina, M. K. and Sharma, M. Indian Council of Medical Research, New Delhi (1976) 101].

Phytochemical investigations of the plant *Asparagus racemosus*, have resulted in isolation and characterization of steroidal glycosides [Ravikumar, P. R., Soman, R., Chetty, G. L. Pandey, R. C. and Sukhdev, *Indian J Chem.* 26 B (1987) 1012, Kar, Deepak Kumar and Sen Sumitra, *Cell Chromosome Res.* 7 (1984) 10], a novel cage type pyrrolizidine alkaloid, asparaginine [Sekine, T., Fukasawa, N., Kashiwagi, Y., Ruangrungsi, N. and Murakoshi, I. *Chem. Pharm. Bull.* 42 (1994) 1360] and a 9,10-dihydrophenanthrene derivative [Sekine, T., Fukasawa, N., Murakoshi, I. and Ruangrungsi, N. *Phytochemistry*, 44 (1997) 763].

OBJECTS OF THE INVENTION

The main object of the present invention is to provide a novel oligospirostanoside.

Yet another object of the present invention is to provide a process for isolation of a novel oligospirostanoside from *Asparagus racemosus*.

Another object of the invention is to provide and characterize a novel sarsasapogenin glycoside Immunoside, an oligospirostanoside isolated from aqueous extract of *Asparagus racemosus*, present in the range of 0.0023–0.0045% w/w in the dried plant material.

SUMMARY OF THE INVENTION

Accordingly, the present invention provides a novel oligospirostanoside of formula 1,3-0-[α-L-rhamnopyranosyl-(1→2)-α-L-rhamnopyranosyl-(1→4)-0-β-D-glucopyranosyl]-25(S)-5β-spirostan-3β-ol of the formula 1 below:

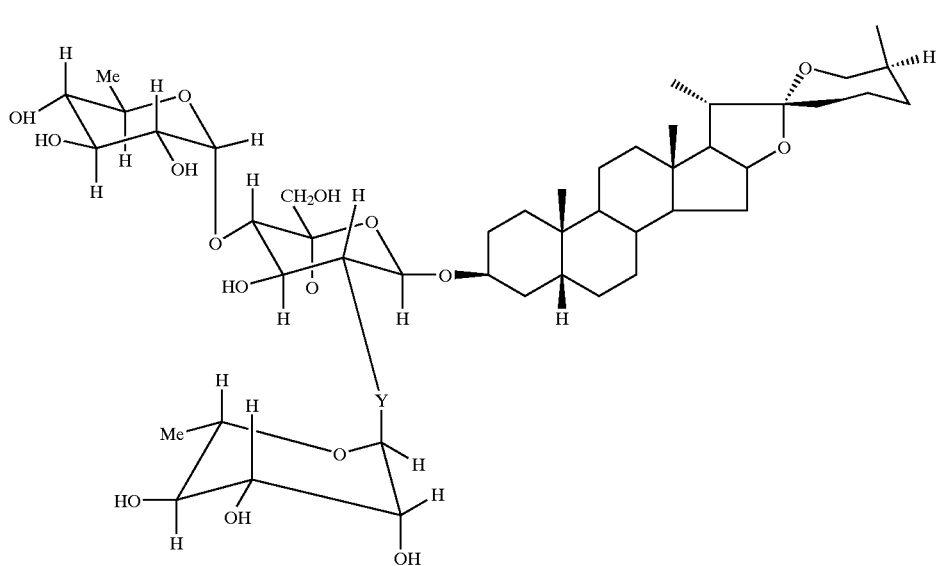

FORMULA 1

The present invention also relates to a process for isolation of immunoside, 3-rhamnopyranosyl-(1→2)-α-L-rhamnopyranosyl-(1→4)-0-β-D-glucopyranosyl]-25(S)-5β-spirostan-3β-ol of the formula 1 below which comprises:

FORMULA 1

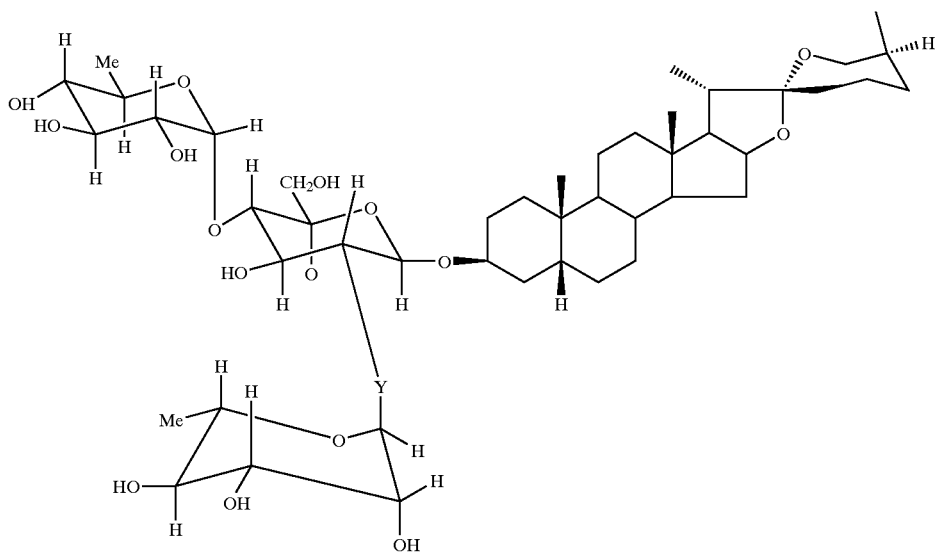

The present invention also relates to a pharmaceutical composition comprising an effective amount of the novel oligospirostanoside 3-0-[α-L-rhamnopyranosyl-(1→2)-α-L-rhamnopyranosyl -(1→4)-0-β-D-glucopyranosyl]-25(S) 5β-spirostan-3β-ol contained in a pharmaceutically acceptable carrier.

In one embodiment of the invention, the amount of 3-0-[α-L-rhamnopyranosyl-(1→2)-α-L-rhamnopyranosyl-(1→4)-0-β-D-glucopyranosyl]-25(S)5β-spirostan-3β-ol is in the range of 0.006 to 0.0125 mg per kg of body weight of subject to be treated.

The present invention also provides a method for immunomodulation in a immune suppressed animal comprising administering a pharmaceutically effective amount of 3-0-[α-L-rhamnopyranosyl -(1→2)-α-L-rhamnopyranosyl-(1→4)-0-β-D-glucopyranosyl]-25(S)5β-spirostan-3β-ol.

In one embodiment of the invention, the amount of 3-0-[α-L-rhamnopyranosyl-(1→2)-α-L-rhamnopyranosyl-(1→4)-0-β-D-glucopyranosyl]-25(S)5β-spirostan-3β-ol administered to the said animal comprises 0.006 to 0.0125 mg per kilogram of body weight of the animal.

The invention also relates to use of 3-0-[α-L-rhamnopyranosyl-(1→2)-α-L-rhamnopyranosyl-(1→4)-0-β-D-glucopyranosyl]-25(S)5β-spirostan-3β-ol for the preparation of a pharmaceutical composition for immunomodulation in animals.

DETAILED DESCRIPTION OF THE INVENTION

The process for isolation of a novel oligospirostanoside of formula 1 which comprises extraction of dried and powdered roots with a polar solvent with or without prior extraction with EtOAc, subjecting aqueous sol. of the desolvented extract to partitioning with $CHCl_3$, EtOAc, n-BuOH and resolution of n-BuOH extract residue to adsorption/gel permeation chromatography using isotropic or graded elution, reverse phase purification on Lichroprep RP-8 and repeated crystallizations from methanol or ethanol. Physical constants and spectral data ($^1H$—NMR, $^{13}C$—NMR, MS and I R spectral data) are used for characterization of novel isolate. Corroboration of assigned structure is done by permethylation and hydrolysis to get aglycone and partially methylated sugars to confirm linkage site and sequence of sugar units.

Estimation of the compound in the dried plant material is carried out by HPTLC densitometer scanning (0. 0023–0.0045%). The compound of the invention can be used for authentication of immunomodulatory formulation from Asparagus racemosus. The novel oligospirostanoside was evaluated for immunomodulatory activity and the results are given in Table 1. The compound of the invention is obtained as a white amorphous powder, mp 275° C., $[\alpha]_D^{21}$ –90.2[C 0.5% pyridine], molecular composition $C_{45}H_{74}O_{16}$ derived from FABMS, MS $(M+Na)^+$ m/z 893, elemental analytical data and $^{13}C$—NMR, CPD and DEPT spectral data. Immunoside responded positively to the Liebermann-Burchard Reaction [Liebermann, G. (1885) Ber. Deut. Chem. Ges. 18, 1804; Burchard, H. (1890) Chem. Zentbl. 1, 25], negatively to the Ehrlich test [Kiyosawa, S and Hutoh, M. (1968) Chem. Pharm. Bull. 16, 1162; Tschesche, R; Siedel, L., Sharma, S. C. and Wulff, G. (1972) Chemische Berichte, 105, 3397] and positively to Molisch's test indicating it to be spirostanol glycoside.

The following examples for the process of extraction are given by way of illustrations and therefore should not be construed to limit the scope of present invention:

EXAMPLE 1

Dried underground part of plant material Asparagus racemosus (1 Kg) was ground to a coarse powder. Coarse powder was extracted with deionised water at 98° C. for 2 hrs. Extraction process was repeated thrice using total water (7+4+4 Litre, three extractions) in 1:15 ratio w/v with respect to the plant material. All the three extracts were pooled. The pooled aqueous extracts were centrifuged, clear supernatant was evaporated to dryness on a wiped film evaporator at 50±5° C. residue 480 g (extractive value 48%). Aqueous extract residue was dissolved in deionised water (4 Litre) and the resulting solution was extracted with $CHCl_3$, EtOAc and n-BuOH (6×1 Litre each) successively. $CHCl_3$ and EtOAc extracts were 0.2 and 0.3 gm respectively whereas n-BuOH extract residue (40 gm) was rich in quantity and chemical constituents. n-BuOH extract was subjected to adsorption chromatography. 31.0 g of n-BuOH extract dissolved in minimum quantity of MeOH, was adsorbed on $SiO_2$ gel, 100–200 mesh (100 gm) Solvent was completely removed to get free flowing material. A glass column of 1½" dia. was packed with 300 gm $SiO_2$ gel, 100–200 mesh in $CHCl_3$. The adsorbed extract was charged in the column. The column was eluted with solvents by gradually increasing the % age of MeOH in $CHCl_3$ In all 105 fractions of 100 ml each were collected and pooled on the bases of TLC patterns using $EtOAc:MeOH:H_2O::75:13.5:10$ as developing solvent. Spots were visualised by spraying with 1% cericammonium sulphate followed by heating at 110° C. for 20 minutes. Fractions 23–29 showed same TLC pattern. These fractions were pooled, dried and subjected to rechromatography using 100–200 mesh $SiO_2$ gel column (1:20 ratio) and eluted with $CHCl_3$: MeOH mixtures of increasing polarity. In all 60 fractions of 200 ml each were collected. Fractions 37–44 were pooled on the bases of TLC and again subjected to chromatography. 30 fractions of 100 ml each were collected. Fractions 23–28 were concentrated under reduced pressure. Residue was repeatedly crystallised from MeOH, a colourless amorphous powder soluble in $CHCl_3$: MeOH mixture was obtained. Compound Rf 0.53, (solvent system $EtOAc:MeOH:H_2O::75:13.5:10$) was named as immunoside.

EXAMPLE 2

Air-dried roots (1 Kg) of *A. racemosus* Willd. were ground and extracted with 75% aqueous methanol three times (75% MeOH, 3×5 Litre) for 12 hrs. each. The combined extracts were concentrated to dryness under reduced pressure. The residue (407 gm) was dissolved in water (4 litre) and extracted successively with EtOAc and n-BuOH (6×1 Litre each) to yield the corresponding fractions (0.3 gm, 38 gm). The n-BuOH extract was chromatographed on a column of silica gel (60–120 mesh) eluted with a gradient of MeOH in $CHCl_3$. The $CHCl_3$: MeOH (5:1) eluate was rechromatographed on a silica gel (100–200 mesh) column using $CHCl_3$—MeOH: $H_2O$ (6:1:0.1) as solvent. Fractions homogeneous on TLC were pooled, dried and charged on a sephadex LH-20 column, eluted with MeOH to produce two fractions of 500 ml each. Second fraction containing mainly the target compound was subjected to further purification over Lichroprep RP-8 CC eluted with $MeOH: H_2O$ (3:2) to afford a fraction, which on repeated crystallisation from EtOH yielded a colourless amorphous powder soluble in $CHCl_3$—MeOH mixture. Compound Rf 0.53 (solvent system $EtOAc:MeOH:H_2O::75:13.5:10$) was named as immunoside.

EXAMPLE 3

*A. racemosus* root powder (4 Kg) was extracted with EtOAc (12L×2) in a Soxhlet for 36 hr. each The marc was next extracted with 80% aq. ethanol (10 L×2) for 24 hr. each. The aq. alcoholic extract was distilled under reduced pressure to dryness. The residue (700 g) was dissolved in water (1 L) and extracted with n-BuOH saturated with water (250 ml×8). The combined BuOH extractions were desolvented to get saponin mixture (46 gm.) The mixture was subjected to column chromatography over neutral $Al_2O_3$ using n-BuOH saturated with water as the packing solvent and eluent to get six major fractions (500 ml each). Fractions were monitored on TLC using $CHCl_3:MeOH:H_2O::65:35:10$; (lower phase) as developing solvent. Spots were visualised by spraying the plate with 1% cericammonium sulphate followed by heating at 110° C. for 20 minutes. Residues from fractions, 3 and 4 were pooled and chromatographed on ODS silica gel eluting with $MeOH: H_2O$ (3:2) to give two fractions of 350 ml. each. Residue from $2^{nd}$ fraction was subjected to flash CC on $SiO_2$ gel (230–400 mesh) eluting with $CHCl_3:MeOH:H_2O$ (30:10:1) to give the desired compound with traces of impurities. Final purification was achieved by repeated crystallisations from MeOH to get colourless amorphous powder soluble in $CHCl_3$—MeOH mixture. Compound Rf 0.53 (TLC developing system: $EtOAc:MeOH:H_2O::75:13.5:10$) was named as immunoside.

Immunoside, white amorphous powder, mp 275° C., $[\alpha]^{21}$ −90.2 [C 0.5% Pyridine], MS: $^D$FABMS, $[M+Na]^+$ m/z 893. Molecular composition derived to be $C_{45}H_{74}O_{16}$ from MS and elemental analytical data [calcd for $C_{45}H_{74}O_{16}$: C, 62.06; H, 8.50; Found: C. 61.98; 8.47] and $^{13}C$—NMR, CPD and DEPT. The IR spectrum of the saponin indicated the existence of hydroxyl groups (3400–3350 $cm^{-1}$) and the characteristic absorption bands of (25S)-spiroketal at 919 and 896 $cm^{-1}$ with the absorption at 919 $cm^{-1}$ being of greater intensity than at 896 $cm^{-1}$ [Wu G, Jiang S, Jiang F, Zhu D, Wu H and Giang C. (1996) *Phytochemistry* 42, 1677; Li X C, Wang D Z and Yang C R, (1990). *Phytochemistry* 29, 3899]. 25(S)-Spirostane skeleton of Immunoside was also suggested by the occurrence of a resonance at δ109.85 (C-22) in $^{13}C$—NMR spectrum. In addition, $^1H$ and $^{13}C$—NMR (200.13 MHz and 50.32 MHz, $C_5D_5N$) spectra displayed three anomeric proton signals at 4.87 (d, J=7.7 Hz, 1H), 5.73 (brs, 1H) and 6.40 (brs, 1H) corresponding to three anomeric C-atoms at δ101.60, 102.23 and 103.01 respectively indicating that Immunoside contained one glucosyl and two rhamnosyl units in the oligosaccharide function. The anomeric configuration of the glucosyl unit was indicated to be β based on $J_{1,2}$ (7.7 Hz). The anomeric configuration of two rhamnosyl units was assigned on α based on there C-5 chemical shifts at δ69.52 and 70.57 respectively [Soe, S., Tomita, Y., Toti, K. and Yoshimura, Y, *J. Am. Chem. Soc.* 100 (1978)3331]. A comparison of $^{13}C$-Chemical shifts of the sugar units with those reported for methylglycopyranosides revealed glycosylation shifts by δ+6.00 for C-2 and +6.79 for C-4 of glucose unit, thus indicating the presence of one 2,4-disubstituted glucose unit. These data indicated that 2-rhamnose units are linked to glucose moiety at position 2- and 4- . Further proof to the site of interlinkage amongst sugar units and to the sapogenin was provided by hydrolysis of permethylated Immunoside [Hakomori, *S., J. Biochem.* 55 (1964)205]. Acid catalyzed hydrolysis of per-methylated Immunoside yielded sapogenin, 3,5,6-tri-0-methyl-D-glucose and 2,3,4-tri-0-methyl-L-rhamnose. This established linkage of two α-L-rhamnose units to glucosyl moiety as 1→2 and 1→4. The sapogenin was identified as sarsasapogenin by direct comparison on TLC, mmp, co—ir with authentic sample. These data confirm the presence of construct Immunoside as 3-0-[α-L-rhamnopyranosyl-(1→2)-α-L-rhamnopyranosyl-(1→4)-0-β-D-glucopyranosyl]-25(S)5β-spirostan-3β-ol, a new chemical entity.

Biological Activity

Oral administration of Immunoside potentiated antibody synthesis and enhanced cell-mediated immune response in immunecompromised experimental animals by 55.55–69.44% and 77.77–102.22% respectively in dose levels of 0.0062–0.0125 mg Kg$^{-1}$ (Table 1). The draft spectroscopy data (IR; $^1$H, $^{13}$C—NMR, MS) along with physical constants (mp, $[\alpha]_D^{21}$) result in the characterization of the novel molecule as 3-0-[α-L-rhamnopyranosyl-(1→2)-α-L-rhamnopyranosyl- 1→4)-0-β-D-glucopranosyl]-25(S)-5β-spirostan-3β-ol. The assigned structure was corroborated by chemical degradation data i.e., permethylation and hydrolysis. The immunomodulatory activity, both in humoral and CMI models, of the compound has been evaluated in the product.

TABLE 1 effect of immunoside on humoral and cell mediated immune response in immunecompromised mice

| Treatment | Dose mg/kg p.o. | Antibody titre mean ± S.E. | % change compared to control | DTH mean ± S.E. | % change compared to control |
|---|---|---|---|---|---|
| Control | — | 6.66 ± 0.24 | — | 0.58 ± 0.15 | — |
| Cyclo | 250 | 3.60 ± 0.33 | 45* | 0.45 ± 0.24 | 23* |
| AR-Iv | 0.0006 | 5.60 ± 0.33 | 56** | 0.80 ± 0.14 | 78*** |
|  | 0.0125 | 6.41 ± 0.16 | 78*** | 0.91 ± 0.42 | 102*** |
| LEV | 2.5 | 6.80 ± 0.30 | 89*** | 1.08 ± 0.14 | 140*** |

Cyclo: Cyclodextrin; AR-IV: 3-0-[α-L-rhamnopyranosyl-(1→2)-α-L-rhamnopyranosyl-(1→4)-0-β-D-glucopyranosyl]-25(S)-5β-spirostan-3β3-ol.
LEV: Levamisole;
DTH: Delayed type hypersensitivity
Number of observations: 12
*P < 0 05;
**P < 0.01;
***P < 0.001

Treatment Schedule 0 day: sensitization with 0.2 ml of 5×10$^9$ SRBC/ml i.p.

0–4 day: drug treatment

4$^{th}$ day: challenged with 20 μl of 5×10$^9$ SRBC/ml into right hind footpad for DTH reaction only.

SRBC: Sheep red blood cell.

5$^{th}$ day: measurement of foot thickness/Haemagglutination antibody titre

We claim:

1. Process for the isolation of novel oligospirostanoside 3-0-[α-L-rhamnopyranosyl-(1→2)-α-L-rhamnopyranosyl-(1→4)-0-β-D-glucopyranosyl]-25(S)-5β-spirostan-3β-ol which comprises:

(a) extracting dried and powdered roots of *Asparagus racemosus* with a polar solvent selected from the group consisting of water, methanol, ethanol and any mixture thereof with or without prior extraction with EtOAc, (b) clarifying the extract obtained above in step (a), (c) removing the solvent from the clarified extract obtained from step (b) to obtain a dry residue, (d) dissolving said dry residue in water and subjected the solution to partitioning with CHCl$_3$, EtOAc and n-BuOH sequentially or n-BuOH saturated with water alone to obtain an alcoholic extract, (e) subjecting said alcoholic extract to distillation under reduced pressure to get a dry residue, and (f) resolving the dry residue to obtain pure constituents and separating the constituents to obtain 3-0-[α-L-rhamnopyranosyl-(1→2)-α-L-rhamnopyranosyl-(1→4)-0-β-D-glucopyranosyl]-25(S)-5β-spirostan-3β-ol.

2. Process as claimed in claim 1 wherein oligospirostanoside obtained is of the formula 1 below

FORMULA 1

3. Process as claimed in claim 1 wherein clarified extract is obtained by filtration or centrifugation.

4. Process as claimed in claim 1 wherein the clarified extract is spray dried, dried in a hot air oven or dried in a rotavapour at 50±5° C.

5. Process as claimed in claim 1 wherein the dry residue of step (e) is resolved into pure constituents in step (f) by adsorption gel permeation chromatography using isotropic or graded elution, reverse phase purification on Lichroprep RP-8 or pooling and distillation of TLC homogeneous fractions under reduced pressure.

6. Process as claimed in claim 1 wherein the dry residue obtained at the end of step (e) is repeatedly crystallized using methanol or ethanol to get purified oligospirostanoside.

* * * * *

UNITED STATES PATENT AND TRADEMARK OFFICE
CERTIFICATE OF CORRECTION

PATENT NO.    : 6,670,459 B2
DATED         : December 30, 2003
INVENTOR(S)   : Handa et al.

It is certified that error appears in the above-identified patent and that said Letters Patent is hereby corrected as shown below:

<u>Title page,</u>
Item [73], Assignee, before "Zandu Pharmaceutical Works Ltd., Maharashtra, (IN)" please add -- Council of Scientific and Industrial Research, New Delhi (IN) -- and -- Department of Science and Technology, New Delhi (IN) --.

Signed and Sealed this

Eighteenth Day of May, 2004

JON W. DUDAS
*Acting Director of the United States Patent and Trademark Office*